US00PP28032P3

(12) United States Plant Patent
Van Dijk

(10) Patent No.: US PP28,032 P3
(45) Date of Patent: May 16, 2017

(54) ***ANTHURIUM* PLANT NAMED 'ANTHCUFPA'**

(50) Latin Name: ***Anthurium andreanum* L.**
Varietal Denomination: ANTHCUFPA

(71) Applicant: ANTHURA B.V., Bleiswijk (NL)

(72) Inventor: Jan Van Dijk, Bleiswijk (NL)

(73) Assignee: ANTHURA B.V., Bleiswijk (NL)

( * ) Notice: Subject to any disclaimer, the term of this patent is extended or adjusted under 35 U.S.C. 154(b) by 49 days.

(21) Appl. No.: 14/545,990

(22) Filed: Jul. 15, 2015

(65) Prior Publication Data

US 2017/0020052 P1 Jan. 19, 2017

(51) Int. Cl.
*A01H 5/02* (2006.01)

(52) U.S. Cl.
USPC ..... Plt./365

(58) Field of Classification Search
USPC ..... Plt./365, 366
See application file for complete search history.

(56) References Cited

PUBLICATIONS

Upov Pluto Plant Variety Database Oct. 25, 2016 for *Anthurium* Anthcufpa, retrieved on Oct. 25, 2016, retrieved from the Internet at <https://www3.wipo.int/pluto/user/en/index.jsp> one page.*

EU Community Pant Variety Rights Application No. 2013/2912, Application n°A201302086, filed Nov. 18, 2013, 7 pages.

EU Community Plant Variety Office Official Gazette, Jan. 2014, Feb. 15, 2014, cover page and pp. 28, 47.

Anthura *Anthurium*: Cut flower and pot plant culture, published Nov. 2014, cover page and pp. 36, 47.

EU Community Plant Variety Rights Grant No. EU 41015, issued May 26, 2015, 2 pages.

Anthura *Anthurium* catalogue: Cut flower and pot plant 2015/2016, published May 2015, cover page and pp. 41, 58.

* cited by examiner

*Primary Examiner* — June Hwu

(74) *Attorney, Agent, or Firm* — Jondle & Associates, P.C.

(57) ABSTRACT

A new and distinct variety of *Anthurium* plant named 'ANTHCUFPA' particularly distinguished by having glossy dark red-purple, very durable spathes that retain the original color for a long period of time, dark green, durable and glossy leaves, flowering continuously throughout the year, a freely branching growth habit and a plant height of 35 cm to 40 cm, is disclosed.

3 Drawing Sheets

Genus and species: *Anthurium andreanum* L.
Variety denomination: 'ANTHCUFPA'.

BACKGROUND OF THE NEW PLANT

The present invention comprises a new and distinct variety of *Anthurium*, botanically known as *Anthurium andreanum* L., and hereinafter referred to by the variety name 'ANTHCUFPA'. The new variety originated from a hybridization made in October 2003 in Bleiswijk, The Netherlands. The female parent was a brown *Anthurium* pot plant designated '6077-01' (unpatented), and the male parent was a brown *Anthurium* plant designated 'ANTHCIMWI' (U.S. Plant Pat. No. 20,255).

A single plant was selected in November 2005 and has been asexually reproduced repeatedly by meristem tissue culture in Bleiswijk, The Netherlands over a ten-year period. The present invention has been found to retain its distinctive characteristics through successive asexual propagations.

Plant Breeder's Rights for this variety have been applied for in the European Union on Nov. 18, 2013 and in Mexico on May 13, 2015. 'ANTHCUFPA' has not been made publicly available or sold anywhere in the world more than one year prior to the filing of this application.

SUMMARY OF THE INVENTION

The following are the most outstanding and distinguishing characteristics of this new variety when grown under normal horticultural practices in Bleiswijk, The Netherlands:

1) Shiny, dark red-purple, cordate spathe;
2) White spadix with green tip;
3) Freely branching growth habit; and
4) Shiny, dark green foliage.

DESCRIPTION OF THE PHOTOGRAPHS

This new *Anthurium* plant is illustrated by the accompanying photographs which show the overall plant habit including blooms and foliage of the plant; the colors shown are as true as can be reasonably obtained by conventional photographic procedures. The photographs are of a 35-week old plant grown in a greenhouse in Bleiswijk, The Netherlands in June 2015.

DESCRIPTION OF THE NEW VARIETY

Figure 1:
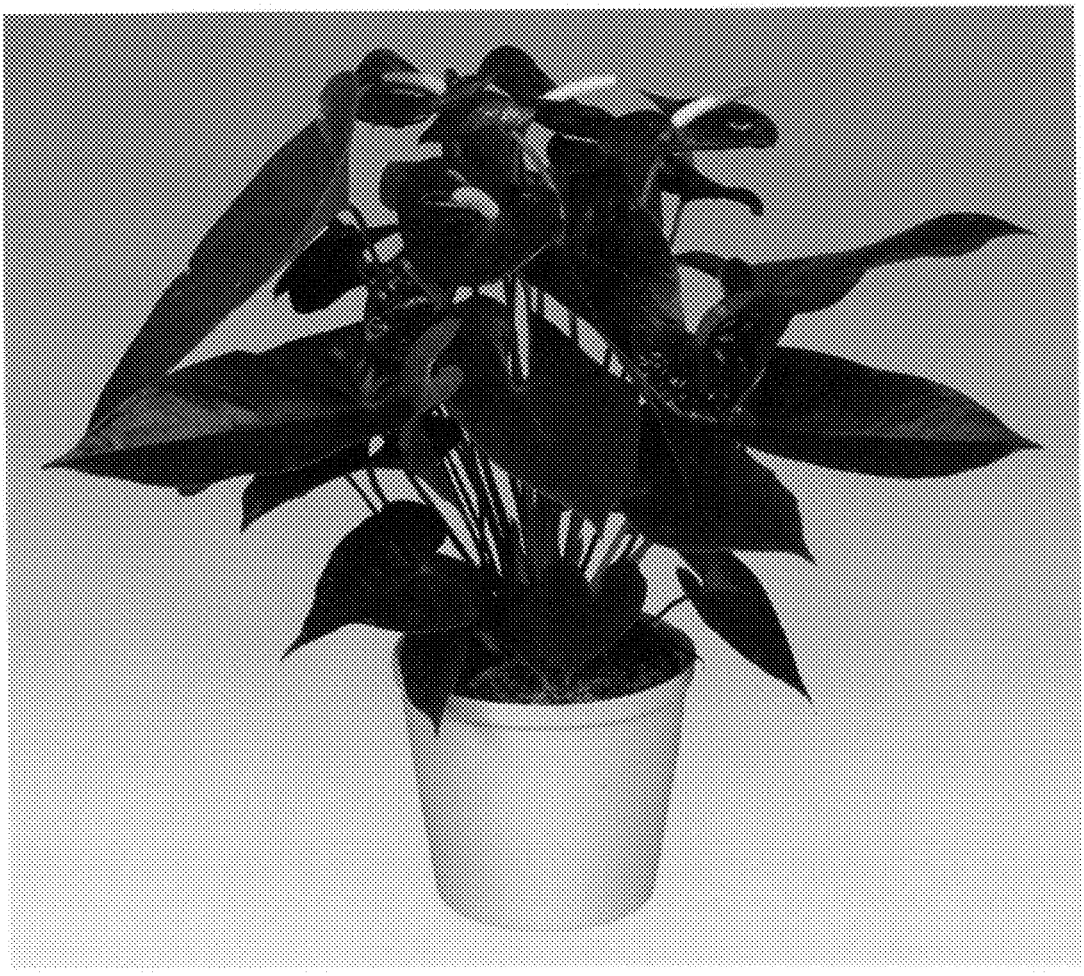
FIG. 1 shows the overall plant habit, including blooms and foliage.
Figure 2:
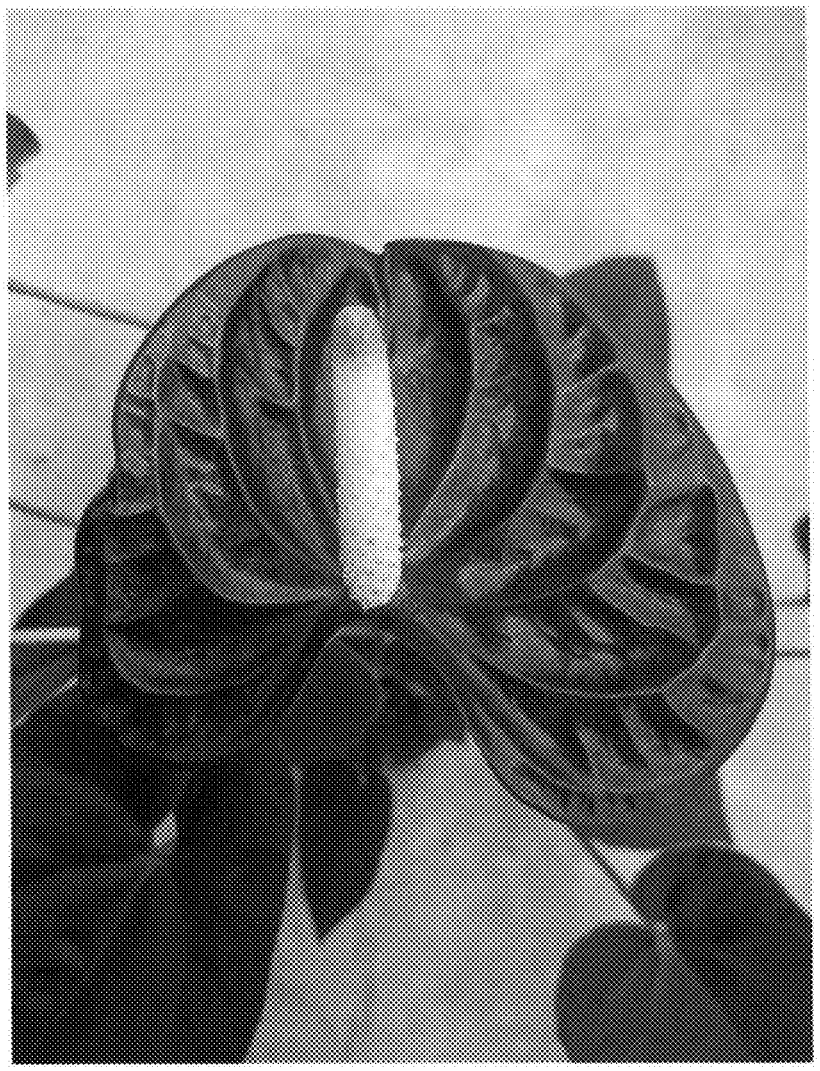
FIG. 2 shows a close-up of the mature spathe.
Figure 3:
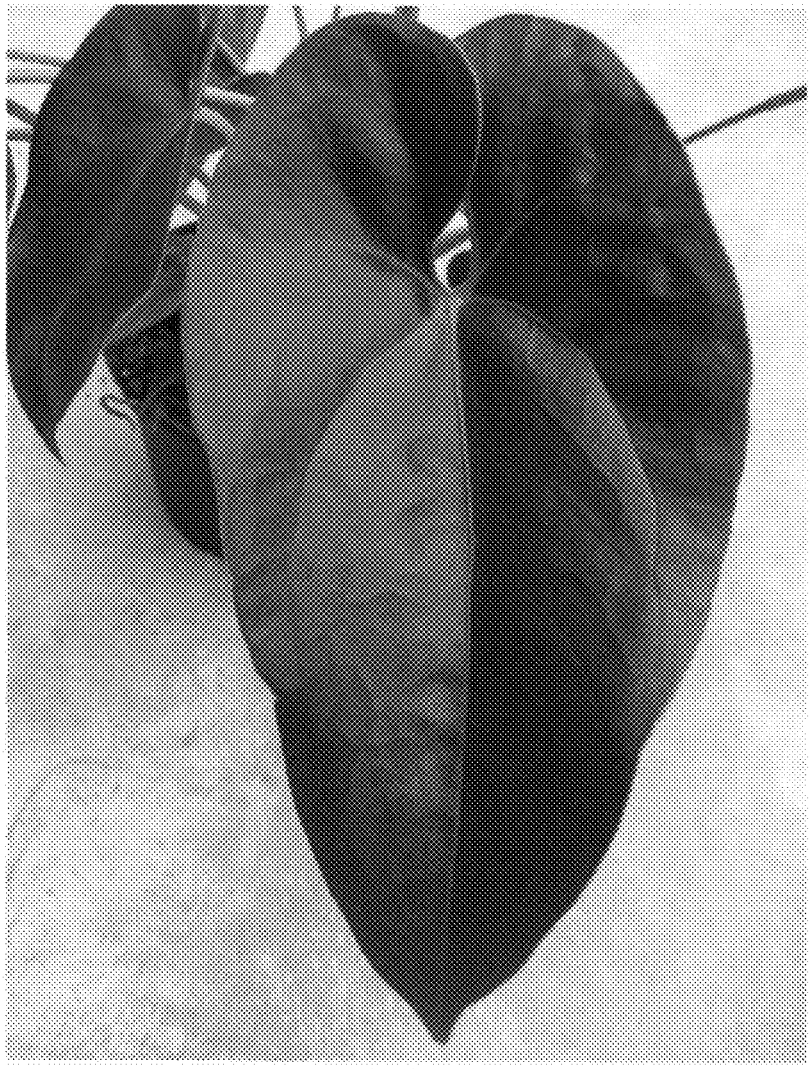
FIG. 3 shows the upper leaf blade surface.

The following detailed description sets forth the distinctive characteristics of 'ANTHCUFPA'. The data which define these characteristics were collected from asexual reproductions carried out in Bleiswijk, The Netherlands. The plant history was taken on 35-week old plants which were planted from tissue culture in 14-centimeter pots and grown in a glass greenhouse between 19° C. and 24° C. Observations were made in June 2015. Color readings were taken under 5000 lux natural light in the greenhouse. Color references are primarily to The R.H.S. Colour Chart of The Royal Horticultural Society of London (R.H.S.) (2001).

DETAILED BOTANICAL DESCRIPTION

Classification:

*Family*.—Araceae.

*Botanical*.—*Anthurium andreanum* L.

*Common name*.—*Anthurium*.

*Demonimation*.—'ANTHCUFPA'.

Parentage:

*Female parent*.—*Anthurium* plant '6077-01' (unpatented).

*Male parent*.—*Anthurium* plant 'ANTHCIMWI' (U.S. Plant Pat. No. 20,255).

Plant:

*Propagation*.—Meristem tissue culture.

*Root description*.—Fleshy light pink colored roots with small hairy lateral roots having yellow-colored root tips.

*Time to produce a finished flowering plant*.—35 to 40 weeks for a 14 cm pot.

*Growth habit*.—Herbaceous perennial; freely branching.

*Height* (*measured from soil, including inflorescence*) .—35.0 cm to 40.0 cm.

*Width* (*measured from leaf tips*).—40.0 cm to 45.0 cm.

Leaves:

*Immature leaves*.—Length: 12.0 cm to 14.0 cm. Width: 6.0 cm to 8.0 cm. Color: Upper surface: RHS 146A. Lower surface: RHS 146A. Texture (both upper and lower surfaces): Shiny.

*Mature leaves*.—Length (fully expanded): 14.0 cm to 21.0 cm. Width: 9.0 cm to 11.0 cm. Shape: Elliptical cordate. Apex: Acuminate. Base: Cordate. Leaf blade angle with the petiole: Between 100 degrees and 110 degrees. Leaf margin: Entire. Color: Upper surface: RHS 139A. Lower surface: RHS 146A. Texture: Shiny, leathery and thick. Venation: Pinnate veining; the mid-vein and primary veins (the veins that radiate out from the junction of petiole and leaf) protrude at the underside of the leaf blade. Venation color: Upper surface: RHS 144B. Lower surface: RHS 145A.

*Lobes*.—Arrangement: Leaf blade has two lobes extending past the petiole. The lobes are overlapping. Length of lobes of mature leaf blades: 3.0 cm to 5.0 cm. Width of lobes of mature leaf blades: 3.0 cm to 4.0 cm. Distance for petiole/leaf junction to highest point on lobes of mature leaf blades: 3.0 cm to 4.0 cm.

*Petiole*.—Cross-section: Round. Diameter: 0.2 cm to 0.3 cm. Length: 18.0 cm to 24.0 cm for a mature leaf size. Color: Mature leaf: RHS 144A. Immature leaf: RHS 144C. Cataphyll color surrounding the petiole: Outside: RHS 146C. Inside: RHS 145C.

*Geniculum*.—Length: 1.5 cm to 2.5 cm. Width: 0.3 cm to 0.4 cm. Color: RHS 144B.

Inflorescence:

*Arrangement*.—Single.

*Flowering habit* (*length of flowering season*).—Continuous.

*Number of inflorescences per plant*.—5 to 6.

*Fragrance*.—Absent.

*Longevity of inflorescence on plant*.—Over a year.

*Longevity of the flower as a cut flower*.—45 to 55 days.

Spathe:

*Buds*.—The spathe is tightly rolled around the spadix and extrudes from the peduncle sheath. After the spathe is fully open the peduncle elongates some extra centimeters.

*Arrangement*.—Spathe angle with the peduncle is between 90 degrees and 110 degrees; the spathe stands on a wiry peduncle about 3.0 cm to 7.0 cm above the foliage.

*Shape*.—Cordate.

*Apex*.—Mucronate.

*Base*.—Cordate.

*Texture*.—Shiny and slightly blistered.

*Margin*.—Entire.

*Size*.—Length: 5.5 cm to 7.5 cm. Width: 7.5 cm to 10.5 cm.

*Color*.—Just fully open: Upper surface: RHS 187A. Lower surface: RHS 187B.

Peduncle:

*Shape*.—Erect.

*Cross-section*.—Round.

*Length*.—20.0 cm to 30.0 cm.

*Diameter*.—0.2 cm to 0.3 cm.

*Color*.—RHS 144C.

Flowering time:

*General*.—One small rooted untreated tissue culture plant of 2.0 cm tall will flower after 9 to 10 months, depending on the season, and 3 to 4 blossoms appear. More blossoms appear after some additional weeks so that a full flowering and commercial plant will have 5 to 6 dark red-purple spathes. Smaller blossoms may occur on less mature plants.

Spadix:

*Size*.—Length: 3.0 cm to 5.0 cm (depending on flower size). Width (at apex): 0.45 cm to 0.55 cm. Width (at base): 0.7 cm to 0.8 cm.

*Shape*.—Columnar.

*Angle from spadix tip to peduncle*.—140 to 150 degrees.

*Texture*.—When the spathe is unfurling the spadix is smooth. When the spadix matures, small stigmata protrude. The stigmata are evenly distributed round the spadix. The spadix matures from base to top, slowly giving the spadix a somewhat rough appearance.

*Color*.—Immature: RHS 144A. Mature: RHS 155D. Aged: RHS 146A.

Flowers:

*Quantity per spadix*.—150 to 160.

*Spadix flower arrangement*.—Bisexual, rounded in cross-section.

*Shape*.—Rounded.

*Size*.—Length: 0.05 cm to 0.1 cm. Diameter (maximum): 0.1 cm.

*Color*.—RHS 155D.

Reproductive organs:

*Stamens*.—Not visible.

*Pollen amount*.—Very few.

*Pollen color*.—RHS 155D.

*Pistil*.—Quantity: Many. Length: Less than 0.01 cm. Color: RHS 155D.

*Style*.—Not observed.

*Stigma*.—Shape: Ovoid. Diameter: Less than 0.01 cm. Color: RHS 155D.

*Ovary*.—Rarely visible.

*Ovary color*.—Not measured.

Fruit and seed set: None observed.

Disease and pest resistance: Not observed to date.

COMPARISON WITH PARENTAL AND COMMERCIAL VARIETIES

'ANTHCUFPA' differs from the female parent plant '6077-01' (unpatented) in that 'ANTHCUFPA' has a dark red-purple spathe, whereas '6077-01' has a brown spathe.

'ANTHCUFPA' differs from male parent plant 'ANTHCIMWI' (U.S. Plant Pat. No. 20,255) in that 'ANTHCUFPA' has a dark red-purple spathe, whereas 'ANTHCIMWI' has a brown spathe.

'ANTHCUFPA' differs from commercial variety 'ANTHELFI' (unpatented) in that 'ANTHCUFPA' has a dark red-purple spathe, whereas 'ANTHELFI' has a brown spathe. Additionally, 'ANTHCUFPA' has a more blistered spathe than 'ANTHELFI'.

'ANTHCUFPA' differs from commercial variety 'ANTHCAMZIP' (unpatented) in that the immature spadix color of 'ANTHCUFPA' is green, whereas the immature spadix color of 'ANTHCAMZIP' is yellow with a green tip. Additionally, 'ANTHCUFPA' has a dark red-purple spathe, whereas 'ANTHCAMZIP' has a dark red spathe.

I claim:

1. A new and distinct variety of *Anthurium* plant named 'ANTHCUFPA', substantially as illustrated and described herein.

* * * * *